(12) United States Patent
Davis et al.

(10) Patent No.: US 7,312,453 B2
(45) Date of Patent: Dec. 25, 2007

(54) METHODS FOR DETERMINING CORROSION PRODUCTS ON SUBSTRATES USING INFRARED IMAGING

(75) Inventors: Bruce R. Davis, Seattle, WA (US); Paul H. Shelley, Lakewood, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/535,025

(22) Filed: Sep. 25, 2006

(65) Prior Publication Data

US 2007/0020762 A1 Jan. 25, 2007

Related U.S. Application Data

(62) Division of application No. 11/279,309, filed on Apr. 11, 2006, now Pat. No. 7,135,683, which is a division of application No. 10/427,006, filed on Apr. 29, 2003, now Pat. No. 7,057,177.

(51) Int. Cl.
*G01J 5/02* (2006.01)
(52) U.S. Cl. .............................. 250/341.1; 250/339.01; 250/339.06; 250/339.11
(58) Field of Classification Search .................. None
See application file for complete search history.

(56) References Cited

U.S. PATENT DOCUMENTS

| | | | |
|---|---|---|---|
| 3,017,512 A | 1/1962 | Wolbert | |
| 3,733,485 A | 5/1973 | Gaynor et al. | |
| 3,994,586 A | 11/1976 | Sharkins et al. | |
| 4,703,187 A | 10/1987 | Hofling et al. | |
| 4,748,329 A | 5/1988 | Cielo et al. | |
| 4,800,279 A | 1/1989 | Hieftje et al. | |
| 4,985,622 A | 1/1991 | Kessler et al. | |
| 5,091,647 A | 2/1992 | Carduner et al. | |
| 5,244,956 A * | 9/1993 | Miller ........................ | 524/403 |
| 5,289,266 A | 2/1994 | Shih et al. | |
| 5,483,338 A | 1/1996 | Wachter et al. | |
| 5,573,952 A | 11/1996 | Moessner | |
| 6,151,969 A | 11/2000 | Miller et al. | |

(Continued)

FOREIGN PATENT DOCUMENTS

FR 2680240 2/1993

(Continued)

OTHER PUBLICATIONS

Ed. Humecki, Howard. Practical Guide to Infrared Microspectroscopy, Practical Spectroscopy Series vol. 19, McCrone Associates, 1995, pp. 1-6 & 41-42.*

(Continued)

*Primary Examiner*—David Porta
*Assistant Examiner*—Yara B Green
(74) *Attorney, Agent, or Firm*—Lee & Hayes, PLLC

(57) ABSTRACT

Methods for determining corrosion products on a substrate are disclosed. In one embodiment, a non-destructive method for determining an amount of corrosion product on a metallic substrate includes non-destructively determining a value Ia of infrared energy absorbed in a corrosion product on a metallic substrate; and correlating the value Ia of the infrared energy absorbed to an amount of the corrosion product.

19 Claims, 7 Drawing Sheets

U.S. PATENT DOCUMENTS

| | | | |
|---|---|---|---|
| 6,184,528 B1 * | 2/2001 | DiMarzio et al. | 250/339.08 |
| 6,671,047 B2 | 12/2003 | Opsal et al. | |
| 6,675,029 B2 | 1/2004 | Monfre et al. | |
| 6,697,654 B2 | 2/2004 | Lorenz et al. | |
| 6,734,962 B2 | 5/2004 | Treado et al. | |
| 6,794,651 B2 | 9/2004 | Shelley et al. | |
| 6,853,926 B2 * | 2/2005 | Alfano et al. | 702/40 |
| 6,895,360 B2 | 5/2005 | Liu et al. | |
| 6,919,957 B2 | 7/2005 | Nikoonahad et al. | |
| 2003/0020916 A1 * | 1/2003 | Ghilai et al. | 356/445 |
| 2004/0099807 A1 * | 5/2004 | Shelley et al. | 250/339.01 |
| 2005/0098728 A1 | 5/2005 | Alfano et al. | |

FOREIGN PATENT DOCUMENTS

| | | |
|---|---|---|
| WO | WO2004048888 A3 | 6/2004 |

OTHER PUBLICATIONS

Kuzik, L.A. et al.,"Effect of noble metal coating on a natural aluminum oxide film." Thin Solid Films 340 (pp. 288-291) Elsevier Science S.A. 1999.*

Namkung, et al., "Detection of Aluminum Corrosion by Evanescent Wave Absorption Spectroscopy with Optical Fibers." SPIE vol. 2444. (pp. 447-453), 1995.*

Johnston, C. et al., "Measuring the Surface Area of Aluminum Hydroxide Adjuvant." Journal of Pharmaceutical Sciences, vol. 91, No. 7 (pp. 1702-1706), Jul. 2002.*

Anicai, "Analysis of Electrochemical Colored Aluminum Anodic Films in AgNO3-Based Electrolytes by Diffuse Reflectance Spectra," Elsevier Science, Inc., Metal Finishing, pp. 10-13, 1998.

Drukker, et al., "Mechanical and chemical consequences of through thickness thermal gradients in polyimide matrix composite materials," Elsevier, Composites Part A: Applied Science and Manufacturing, www.elsevier.com/locate/composites, pp. 125-133, 2003.

Laet, et al., "Development of an Optical Model for Steady State Porous Anodic Films on Aluminum Formed in Phosphoric Acid," Elsevier, This Solid Films, 320, pp. 241-252, 1998.

Mehrkam, et al., "Detection of Composite Heat Damage By Drift Spectroscopy," 38th International SAMPE Symposium, XP009046905, pp. 217-223, 1993.

Palovic, et al., "Optical and Microstructural Properties of Anodically Oxidized Aluminum," Elsevier Sequoia, Thin Solid Films 138, pp. 97-109, 1986.

Powell, et al., "Nondestructive Inspection of Heat Damage to Graphite-Epoxy Laminates Using Diffuse Reflectance Fourier Transform Infrared Spectroscopy (DRIFTS)," 29th International SAMPE Technical Conference, XP009046906, pp. 766-775, 1997.

"Standard Guide for Preparation of Aluminum Surfaces for Structural Adhesives Bonding (Phosphoric Acid Anodizing)", ASTM International Designation: D 3933-98, Copyright 2003, pp. 3-4, American Society for Testing and Materials, 100 Barr Harbor Dr., West Conshohocken, PA 19428.

* cited by examiner

METHODS FOR DETERMINING CORROSION PRODUCTS ON SUBSTRATES USING INFRARED IMAGING

CROSS REFERENCE TO RELATED APPLICATIONS

This patent application is a divisional application of, commonly-owned U.S. patent application Ser. No. 11/279,309 entitled "Infrared Imaging for Evaluation of Corrosion Test Coupons" filed on Apr. 11, 2006 now U.S. Pat. No. 7,135,683, which is a divisional of U.S. patent application Ser. No. 10/427,006 entitled "Infrared Imaging for Evaluation of Corrosion Test Coupons" filed on Apr. 29, 2003, now issued as U.S. Pat. No. 7,057,177 on Jun. 6, 2006, which applications are incorporated herein by reference.

FIELD OF THE INVENTION

This invention relates generally to measuring corrosion, and more specifically, to measuring the degree and amount of corrosion on a substrate.

BACKGROUND OF THE INVENTION

Corrosion occurs on metals and results in corrosion products. Measurements of the degree and amounts of localized and general corrosion have typically been made by visual inspection with an inspector often relying on his or her experience and on reference cards containing images of surfaces that are corroded to varying degrees. Visual corrosion inspections thus involve a degree of subjectivity.

Corrosion inspection is important for monitoring in-service equipment, structures, and vehicles. Inspection is also important for manufacturing quality control and evaluating the performance of anti-corrosion coatings. In manufacturing quality control, monitoring of the application of anti-corrosion coatings to metal surfaces often is done by periodically coating test coupons of a metal substrate, exposing the coated test coupons to a corrosive environment, and then visually inspecting the test coupons for localized or general corrosion products.

Similarly, in evaluating new corrosion coatings, test coupons are coated with different formulations of the corrosion coatings. These test coupons are exposed to a corrosive environment, and then visually inspected for corrosion products. Such a visual inspection of the test coupons for quality control and for grading coatings after exposure to a corrosive environment involves a degree of subjective judgment by the visual inspector.

Corrosion inspection monitoring, anti-corrosion coating application, and the evaluation of new corrosion coatings are important for many types of equipment, structures, and vehicles exposed to corrosive environments or weathering. By way of example, corrosion control for aircraft constructed with aluminum alloys is important due to the range of environments to which aircraft are exposed to, and the lifetime over which the aircraft are exposed those environments. Currently, corrosion inspection, manufacturing quality control of corrosion coatings application, and evaluation of new corrosion control coatings for aluminum alloys, for aircraft, is performed visually as described above.

Therefore, there exists an unmet need in the art for a non-destructive quantitative means of determining the degree and amounts of localized or general corrosion on metallic substrates.

SUMMARY OF THE INVENTION

The present invention provides methods for non-destructively determining an amount of a corrosion product on a substrate using infrared imaging. The amount of byproducts may represent an objective comparison between relative amounts of and areas of corrosion products on different samples, or may be correlated quantitatively with corrosion product thicknesses or density. Embodiments of the invention may be employed to measure corrosion products over a wide area and quantitatively map the corrosion products over that area. Advantageously, embodiments of the invention may provide an objective, quantitative method for measuring corrosion products on substrates, including metal substrates.

In one embodiment, a non-destructive method for determining an amount of corrosion product on a metallic substrate includes non-destructively determining a value Ia of infrared energy absorbed in a corrosion product on a metallic substrate; and correlating the value Ia of the infrared energy absorbed to an amount of the corrosion product.

In alternate embodiments, the method may further include determining a value Io of infrared energy reflected from the metallic substrate without the corrosion product. The method may further include determining a value Is of infrared energy reflected from the metallic substrate having the corrosion product. Methods in accordance with still other embodiments may further include displaying a map of the amount of corrosion product on the metallic substrate. Displaying may include displaying a contour map, displaying a gray-scale map, displaying a color map, and displaying a 3-dimensional projection.

In accordance with yet another embodiment of the invention, a method for quantifying an amount of a corrosion product on a substrate includes projecting an infrared energy onto at least a portion of the corrosion product on the substrate; non-destructively determining an amount of infrared energy absorbed in the corrosion product on the substrate; and determining the amount of corrosion product on the substrate by correlating the amount of infrared energy absorbed to a set of predetermined absorption values.

BRIEF DESCRIPTION OF THE DRAWINGS

Embodiments of the present invention are described in detail below with reference to the following drawings.

DETAILED DESCRIPTION OF THE INVENTION

The present invention relates to apparatus methods and systems for non-destructively determining an amount of a corrosion product on a substrate using infrared imaging. Many specific details of certain embodiments of the invention are set forth in the following description and in FIGS. 1-7 to provide a thorough understanding of such embodiments. One skilled in the art, however, will understand that the present invention may have additional embodiments, or that the present invention may be practiced without several of the details described in the following description.

By way of example, a non-destructive method is provided for objectively determining an amount of a corrosion product on a metallic substrate. A value of infrared energy reflected from the metallic substrate without corrosion is determined, and a value of infrared energy reflected from the metallic substrate with the corrosion product is determined. A value of infrared energy absorbed in the corrosion product is determined, and the value of the infrared energy absorbed in the corrosion product is correlated to an amount of the corrosion product.

Figure 1:
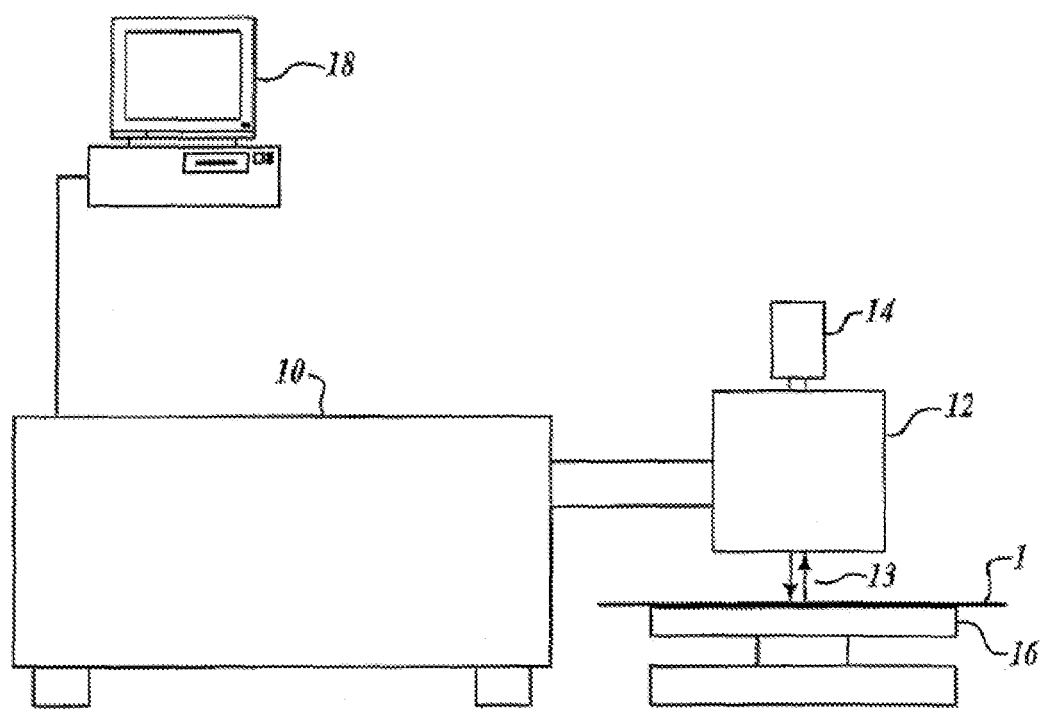
FIG. 1 is a component drawing of an infrared spectroscopy system in accordance with the present invention.

FIG. 1 is a component drawing of an exemplary testing system 5 that may be used to determine an amount of corrosion product according to one presently preferred embodiment of the present invention. An infrared transmission beam 13 is transmitted by an infrared microscope 12, is reflected off a sample 1, and is collected by an infrared microscope 12. It will be appreciated that an infrared source and a collector of the present invention may utilize equipment other than an infrared microscope. Further, the infrared source and the collector and may suitably be independent components. In one presently preferred embodiment, the infrared microscope is a ThermoNicolet Continuum Infrared microscope. In this embodiment, the infrared transmission beam 13 is transmitted to the sample 1 and is reflected off the sample substantially normal to the sample surface. However, it will be appreciated that the infrared transmission beam 13 may be reflected off the sample 1 at angles other than normal to the surface of the sample 1.

The infrared microscope 12 is suitably connected to an infrared spectrometer 10. In an exemplary embodiment, the infrared spectrometer 12 is suitably a ThermoNicolet 760 fourier transform infrared spectrometer.

The sample 1 is held in position on a motorized mapping stage 16 where the sample 1 can be examined by the infrared microscope 12. The mapping stage 16 suitably moves in response to computer control, thereby permitting the sample 1 to be scanned in different areas systematically and automatically. The mapping stage 16 thus allows multiple points on the sample 1 to be examined in sequence by the system 5. It will be appreciated that a mapping stage 16 suitably may be omitted if a small number of sampling points are desired, or if the system 5 is embodied in an infrared imaging system that images an array of points.

The mapping stage 16, as well as the infrared microscope 12 and the infrared spectrometer 10, are suitably controlled by a software application running on a computer 18 attached to the infrared spectrometer 10. In a presently preferred embodiment, the software application for controlling the mapping stage 16, as well as other aspects of the infrared spectroscopy process of the present invention, is a program such as OMNIC/Atlus, distributed by ThermoNicolet.

In a presently preferred embodiment, the infrared microscope 12 includes a CCD infrared collector (not shown) that images a single defined pixel or sample area. It will be appreciated that the system 5 in another preferred embodiment suitably may incorporate an infrared array detector (not shown). The array detector may be located at the focal plane of the infrared microscope 12 or other collector, permitting contemporaneous sampling of infrared absorption at a number of points or pixels simultaneously. In a presently preferred embodiment, the array collector is a focal plane 128×128 array infrared imaging system manufactured by Surface Optics Corporation. In a presently preferred embodiment utilizing a single pixel infrared collector, the infrared microscope and infrared spectrometer system 5 can scan an area of 4 mm×5 mm, with 140 µm×140 µm pixels, in approximately 6½ hours. An array infrared collector implemented with an infrared system suitably may perform the same scanning in approximately 16 seconds, or less, with 70 µm×70 µm pixels. It will be appreciated that other infrared systems are employable with the testing system 5 as desired for a particular application, such as without limitation, non-microscopic infrared spectrometers and infrared imaging systems.

The system 5 of FIG. 1 may be utilized to non-destructively determine the amount of corrosion product on the sample 1. Initially, a base reference value of infrared energy reflected by a clean, uncoated metallic sample (not shown) is determined. The infrared microscope 12 is then used to transmit the infrared transmission beam 13 to a corroded metallic sample 1 to be tested. A comparison is made between the infrared energy of the reflected beam and the infrared energy of the base reference value to determine a corrosion product absorbance value. The resulting corrosion product absorbance value may then be correlated to a corrosion product amount.

In a presently preferred embodiment, the infrared microscope 12 also includes an optical CCD camera 14 that is configured to take an optical image of an area of the sample 1 being examined by the infrared microscope 12. The optical image taken by the CCD camera 14, as well as the infrared information gathered by the infrared microscope 12 operated in conjunction with the infrared spectrometer 10, are transmitted electronically to the computer 18 for further processing and display.

Figure 2:
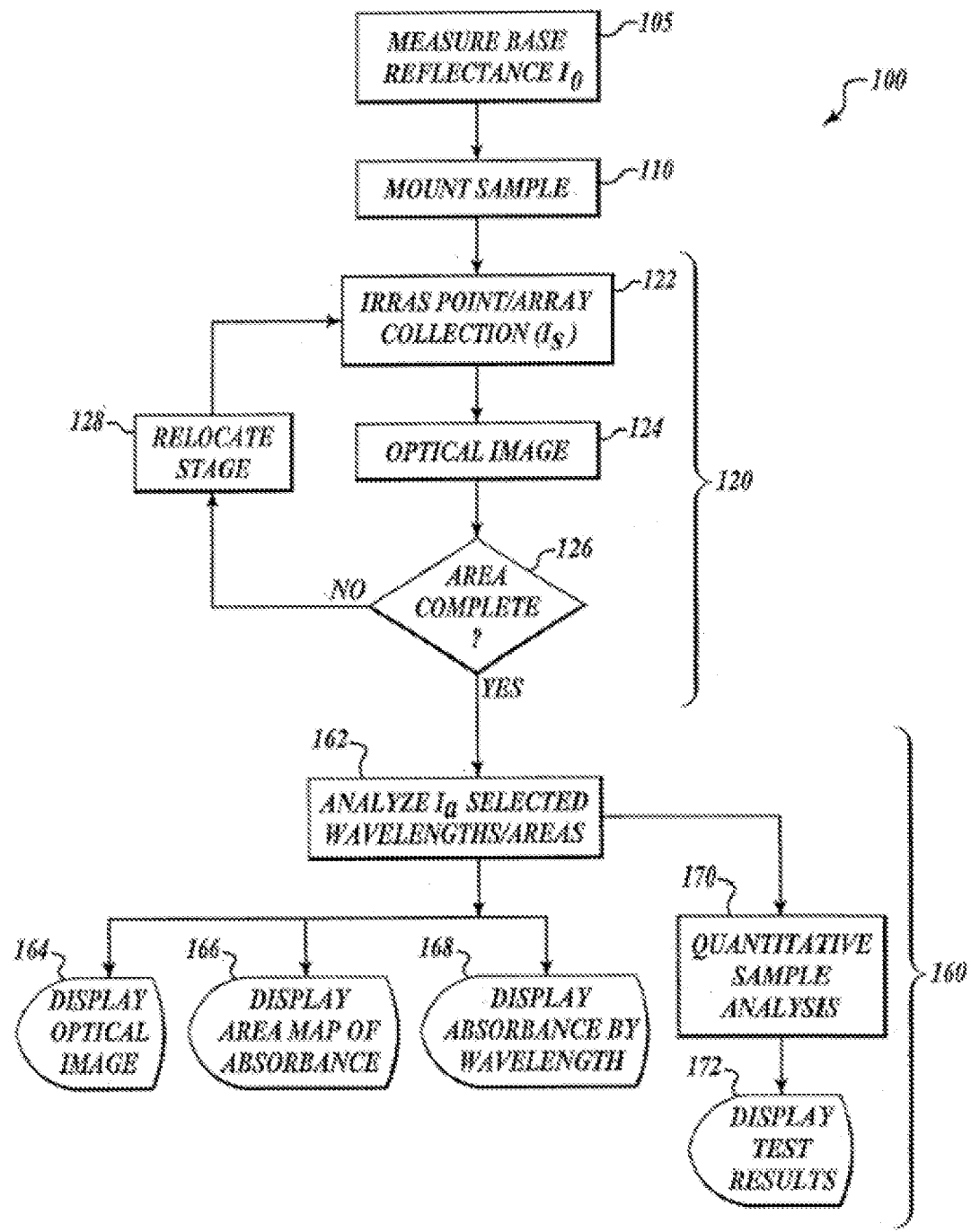
FIG. 2 is a flowchart of an exemplary testing process of the present invention.

Referring to FIG. 2, one presently preferred embodiment of the present invention is implemented through a method 100. At a block 105, base reflectance of a clean metallic substrate is measured over a range of infrared wavenumbers (wavelengths per centimeter). It will be appreciated that the base reflectance of a reference sample (not shown) may be measured at specific frequencies, or over a range of frequencies, depending upon the corrosion products being tested for. The reference sample suitably may be a clean, uncoated reference sample, or any suitable reference, such as in one presently preferred embodiment, gold coated glass.

After the base reflectance of the metallic substrate is measured, a sample being checked for corrosion products is mounted at a block 110. At a segment 120, the sample is scanned. In this exemplary embodiment, scanning of the sample includes performing infrared absorption spectroscopy using a point or array collector at a block 122. In a present embodiment, if desired, an optical image within the visual spectrum may optionally be taken at a block 124 of the sample of the point or array area being sampled. At a decision block 126, a decision is made as to whether or not the infrared absorption spectroscopy examination of the area is complete. If the area is not complete, the motorized stage is relocated at a block 128, and the method 100 returns to the block 122 to perform infrared absorption spectroscopy on an adjoining new point or array area.

At the decision point 126, if the area to be scanned is complete, then the method 100 proceeds to a segment 160 where the collected data is analyzed and displayed. In the segment 160, the infrared spectroscopy results or absorbance values for selected areas of the sample may be analyzed at selected wavelengths or wavelength ranges.

In the process of analyzing the sample at selected wavelengths and areas, an optical image of the area under review may be displayed at a block 164. An area map that shows absorbance of adjoining pixels or sampling areas may be displayed at a block 166. Further, the absorbance of one or more points or areas may be displayed graphically by wavelength at block 168.

Infrared absorbance of a sample suitably is calculated by determining an infrared energy base reference value Io by reflecting an infrared beam off a clean metallic substrate. Determining the base reference value Io occurs at the block 105. The infrared energy spectrum Is of the test sample is determined at the segment 120. In the segment 160, the infrared absorbance value of any corrosion product is calculated at a block 162 by comparing the absorbance of selected wavelengths between the sample and the reference. Analysis of infrared absorption Ia of the corrosion product suitably may include calculation of the absorbance value of the corrosion products using the formula absorbance $Ia = -\log 10(Is/Io)$. Determining Ia at selected wavelengths and areas at the block 162 yields an absorbance value that corresponds to an amount of corrosion product on the sample. The compilation and calculation of Ia is suitably performed in a number of acceptable manners. For example, the calculation may be performed by a computer processor or microprocessor (not shown) arranged to perform mathematical operations. The processor suitably may be included within an infrared spectrometer, within a stand-alone desktop microcomputer, or within circuitry in any suitable device implementing the invention.

In the segment 160, the process of analyzing and displaying the data may include quantitative sample analysis at a block 170. At the block 170, specific quantities of corrosion product may be calculated from absorbance values Ia at points on the sample. Quantitative sample analysis at the block 170 may be suitably based on prior chemical tests and sampling where the absorbance of known quantities of corrosion product on metallic substrate samples have previously been quantified chemically. After quantitative sample analysis at the block 170, the test results showing the quantities of corrosion product determined may be displayed at the block 172.

Figure 3:
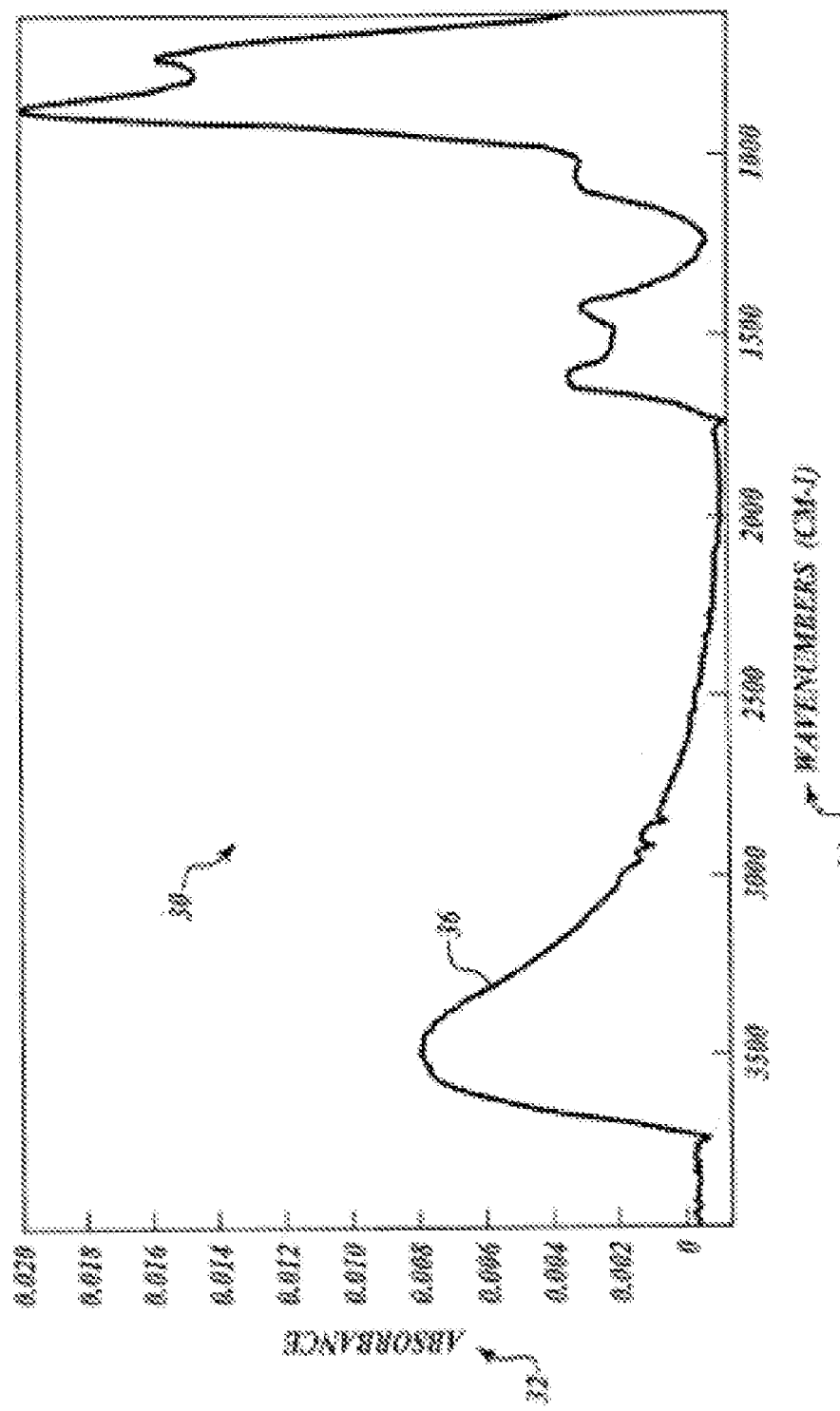
FIG. 3 is a graph of infrared absorbance of aluminum alloy corrosion products.

Metal corrosion products typically exhibit identifiable infrared absorbance curves. By way of example, FIG. 3 is a graph 30 of infrared absorbance of aluminum alloy corrosion products, typically aluminum oxide and aluminum hydroxide. The infrared absorbance of the aluminum corrosion products is graphed as a curve 36 of absorbance 32 versus wavenumber 34. In this example, the aluminum corrosion products exhibit absorbance at around 950 and 1640 wavenumbers (cm−1) for aluminum oxide and at approximately 3400 for aluminum hydroxide.

In an aluminum alloy sample or coupon (not shown) held vertically in a corrosive environment for testing, aluminum oxide and aluminum hydroxide are typically present at a corrosion pit, and aluminum hydroxide commonly forms a streak or tail extending downward from the corrosion pit. As shown in FIG. 3, the absorbance curve 36 for aluminum corrosion products when combined shows a broad peak near 3400 wavenumbers, another peak near 1640 wavenumbers, and a strong narrow peak near 950 wavenumbers.

Figure 4:
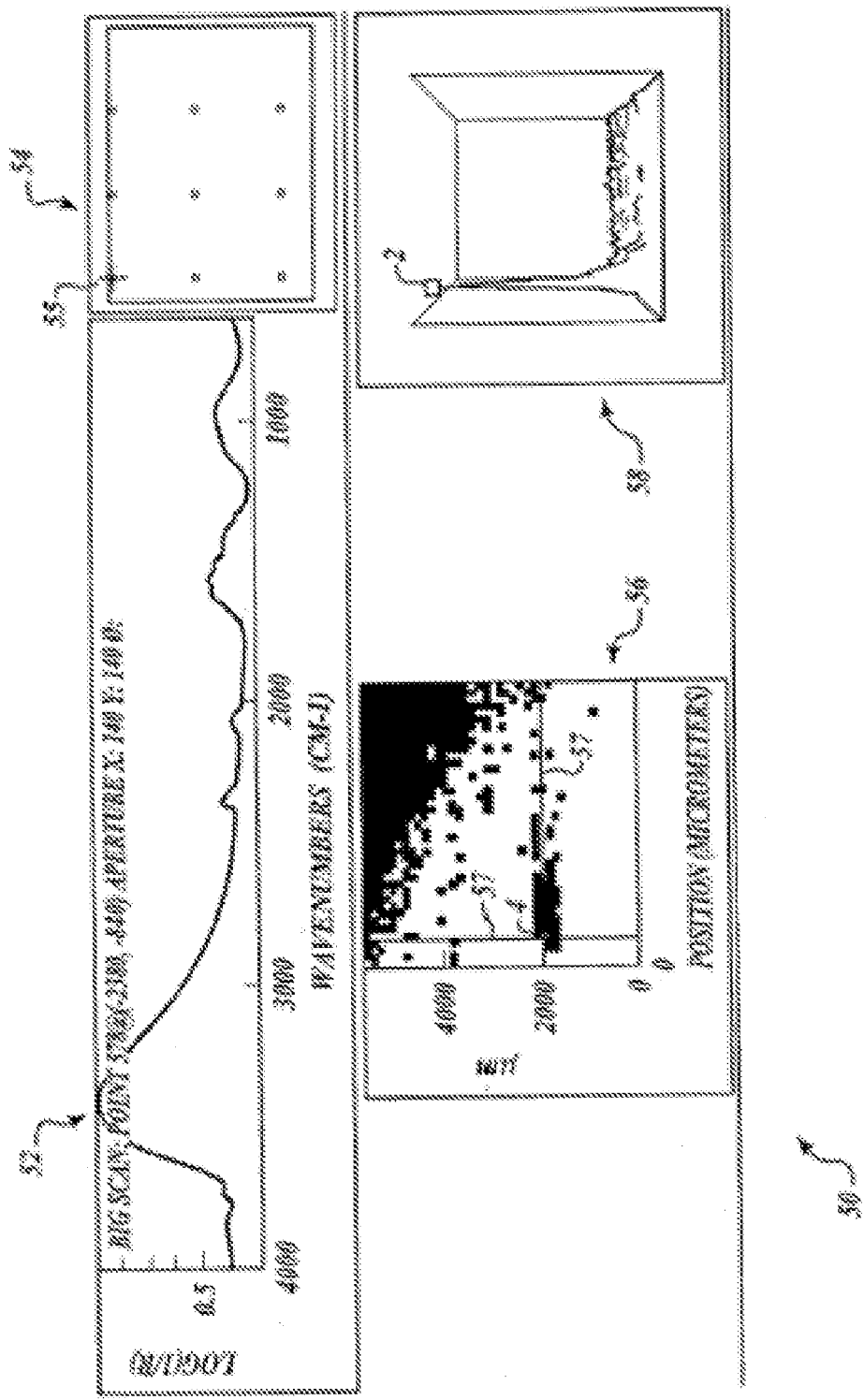
FIG. 4 is a graphical illustration showing infrared absorbance mapping of aluminum corrosion products around a wave number of 950 cm−1.
Figure 5:
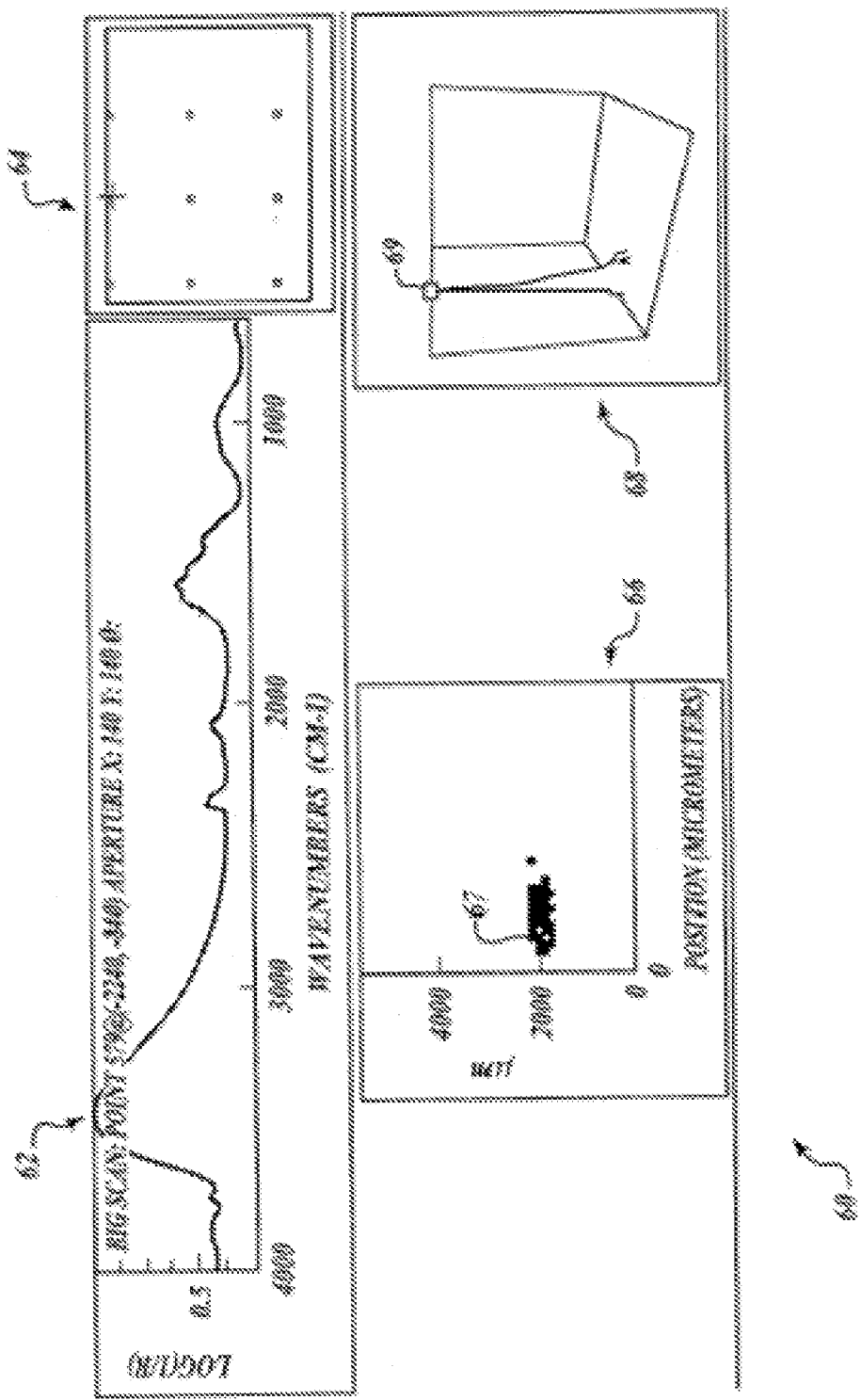
FIG. 5 is a graphical illustration showing infrared absorbance mapping of aluminum corrosion products around a wave number of 1640 cm−1.
Figure 6:
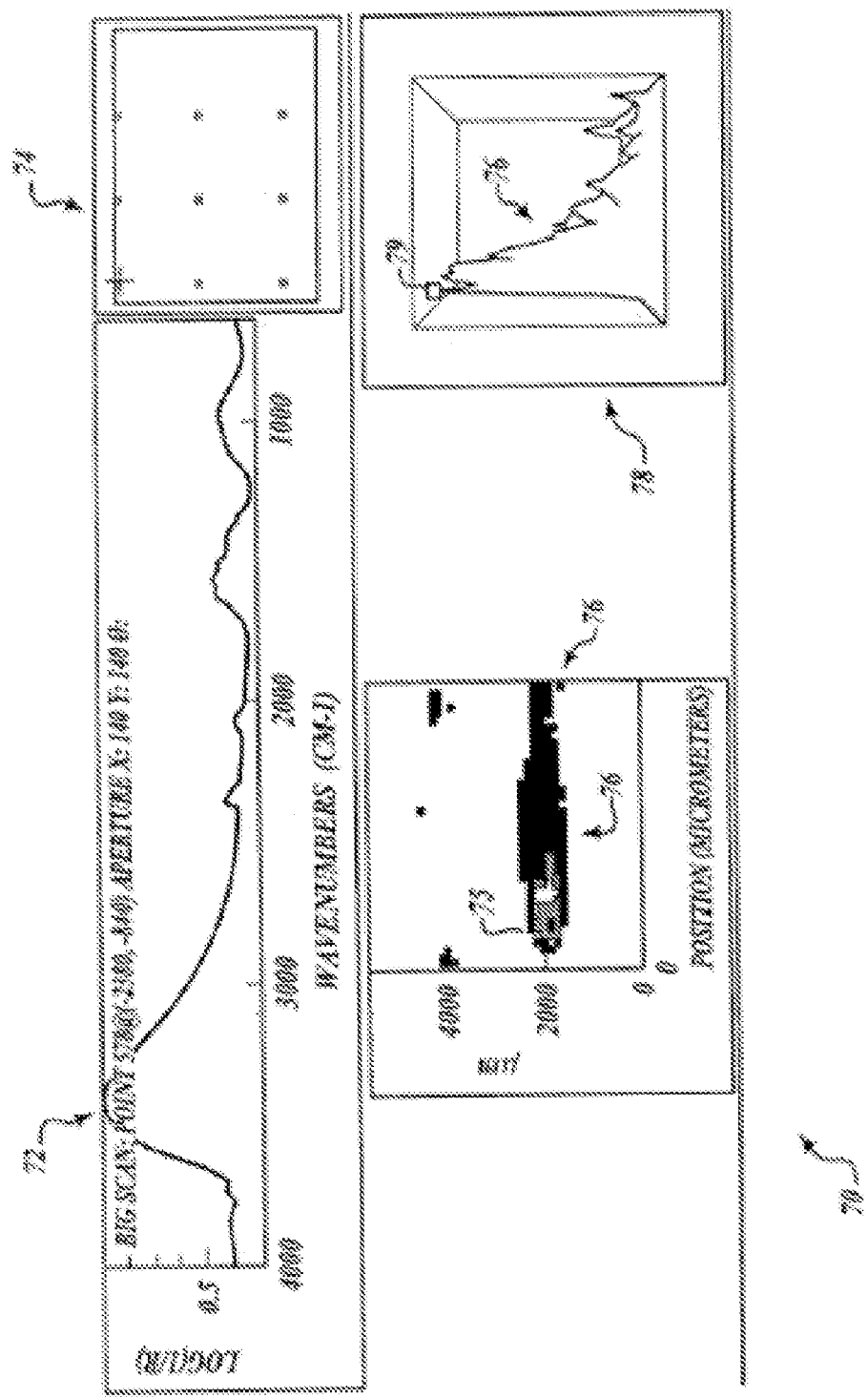
FIG. 6 is a graphical illustration showing infrared absorbance mapping of aluminum corrosion products around a wave number of 3400 cm−1; and, FIG. 7 is a screen shot from a computer application for mapping corrosion products in accordance with the present invention.

FIGS. 4, 5, and 6, reflect the display output of an exemplary computer application and infrared absorption spectroscopy system scanning, by way of example but not limitation, for corrosion products on the same aluminum alloy coupon (not shown) that had previously been exposed to a salt vapor bath. FIG. 4 represents a display of absorbance from scanning near a scan point at wavenumbers around 950 cm−1. FIG. 5 is a display 60 of a nearby scan point at wavenumbers around 1640 cm−1, and FIG. 6 represents a display 70 at the same scan point as FIG. 4 at a wavenumbers around 3400 cm−1. In these three exemplary displays, the scan point or pixel size is 140 µm×140 µm.

FIG. 4 includes an absorbance spectrum 52 over a range of wavenumbers at the designated scan point. The absorbance spectrum 52 is a graph showing absorbance between wavenumbers of approximately 500 and 4000 with absorbance, in this instance calculated as the log 10 of 1 divided by reflectivity (Log (1/R)), graphed on a range of 0.2 to 0.8. The display in FIG. 4 also suitably includes an optical display 54 showing a digital photograph taken in the visual spectrum of the scan point and the surrounding area. The optical display 54 includes a target indicator 55, designating the location of the scan point under review.

The display in FIG. 4 also includes two maps of absorbance at the selected wavenumber at and around the designated scan point. These maps suitably include a pixel map 56 and a three dimensional (3-D) display map 58. The pixel map 56 displays absorbance around a selected wavenumber or range of wavenumbers, in this example, in an area approximately 5000 µm×5000 µm. The pixel map 56 is graphed on an XY plane suitably utilizing a gray scale or color scale to indicated different degrees of absorbance. The pixel map 56 and 3-D map 58 of display 50 of FIG. 4 show absorbance at and around a wavenumber of 950 cm−1. In the 3-D display map 58, absorbance is shown in a three-dimensional projection with absorbance graphed in the Z direction for the scan point and the area surrounding the scan point. In this example, absorbance across an approximately 5000×5000 µm area around the designated scan point is shown in the pixel map 56.

As noted, in FIG. 4, the pixel map 56 and the 3-D display show absorbance at approximately 950 wavenumbers. In these maps in this exemplary embodiment, as well as in the maps of FIGS. 6, 7, and 8, the displayed absorbance at each pixel is computed as an integral of Ia over a designated range of wavenumbers near a selected wavenumber that represents an absorbance peak for the corrosion product being examined.

Integrating Ia over a range of wavenumbers around a peak for the corrosion product under examination averages absorbance errors at any given wavenumber, resulting in more accurate and consistent sampling. The ranges of wavenumbers selected for integrating suitably varies depending upon the 'sharpness' of the absorbance peak of the corrosion product being examined. A sharper peak is captured by a narrower range of wavenumbers than a broader peak. It will be appreciated that a choice of the range for integrating Ia may be somewhat arbitrary as small changes do not affect the overall data. However, it is advantageous to maintain the same range choice over all samples that will be compared with each other. By way of example, but not limitation, suitable ranges for integrating Ia for aluminum alloy corrosion products include 1100 cm−1 to 800 cm−1 about 950 cm−1; 1700 cm−1 to 1400 cm−1, about 1640 cm−1; and 3600 cm−1 to 3200 cm−1 about 34

It will also be appreciated that Ia may be determined or evaluated by peak height. This is suitably done by establishing a baseline on the Ia spectrum between two wavenumbers referred to as baseline wavelengths or baseline points. The peak height is the height in absorbance units of a line dropped from the peak absorbance at a designated wavenumber to the baseline. Ranges for peak height baselines in a presently preferred embodiment, by way of example and not limitation, may be the same ranges as referenced for integrating Ia above, when testing for aluminum alloy corrosion products.

It should be noted that the absorbance spectra 52 in the display 50 in FIG. 4 is the absorbance spectrum for the designated scan point or pixel, displaying absorbance at that pixel over a range of wavenumbers. In contrast, the pixel map 56 and the 3-D display map 58 show absorbance around a single designated wavenumber (or range of wavenumbers integrated into a single absorbance value) over an area including neighboring pixels. Put differently, the display 52 is a graph of absorbance over a range of wavenumbers at a single pixel, while the pixel map 56 and the 3-D map 58 show absorbance at a range of adjoining pixels at a single wavenumber.

In the display 50 of FIG. 4, the scan point for which the absorbance spectrum 52 is shown is at an XY stage location of −2380 μm X, and −840 μm Y, as is listed in the display 50, with a pixel or aperture size of 140 μm×140 μm. The pixel map 56 and the 3-D display map 58 in display 50 of FIG. 4 show absorbance at around wavenumber of 950 at that same scan point −2380 μm X, and −840 μm Y and the area surrounding that scan point. It will be appreciated that aluminum oxide has a strong absorbance peak at around a wavenumber of 950. Absorbance at this scan point is manifested as a peak 2 in the 3-D display map, and a darker area 4 on the pixel map 56. It will be appreciated that this exemplary display 50 is centered around a corrosion pit on an aluminum alloy coupon. The scan point is indicated on pixel map 56 where two crosshairs 57 intersect. Thus, the pixel map 56 and the 3-D map 58 show a peak area of absorbance at and around the scan point at a wavenumber of 950. In FIG. 4, an optical display 54 shows the area around the scan point at visual frequencies. The optical display 54 is a digital photograph of the area around the scan point taken at the time of the scan. In this exemplary embodiment, the area shown in the optical display 54 is smaller than the area shown in the pixel map 56 and the 3-D map 58.

In FIG. 5, the display 60 similarly includes an absorbance spectra 62 at a scan point. In this display, the scan point by way of example is at approximately the same location on the same coupon as the scan point displayed in FIG. 4. The scan point has an X stage position of −2240 μm and a Y stage position −840 μm, again with a pixel size or aperture of 140 μm×140 μm. As in FIG. 4, an optical display 64 shows the area around the scan point at visual frequencies.

In FIG. 5, a pixel map 66 and the 3-D display 68 in the area of the scan point are mapped based upon absorbance at around 1640 wavenumbers. This is within the range of strong absorbance for aluminum hydroxide. In this example, the pixel map 66 shows a darker area 67 reflecting a higher absorbance at wavenumber 1640 at and around the selected scan point. In the 3-D display map 68, the higher absorbance at the wavenumber 1640 in the area surrounding the designated scan point shows as a mound or peak 69. As in FIG. 4, the absorbance at and around the scan point of −2240 μm X, −840 μm Y, reflects corrosion on the aluminum alloy coupon or sample (not shown other than a small portion included in the optical display 64) at this location.

In FIG. 6, the display 70 includes the absorbance spectrum 72 at the scan point. The scan point in display 70 is the same as the scan point in FIG. 4, at −2380 μm X and −840 μm Y on the same sample, again with a pixel size of 140×140 μm. A pixel map 76 and a 3-D display map 78 in display 70 of FIG. 6 show absorbance in the areas surrounding the scan point about a wavenumber of 3400. By way of example, aluminum hydroxide has an absorbance peak at around 3400 wavenumbers. Aluminum hydroxide commonly is present on aluminum alloy samples or substrates in tails or streaks located physically below corrosion pits. When a corrosion pit forms in a corrosive environment, a corrosion tail or streak typically forms physically below the corrosion pit where the corrosion products have been transported to downhill, by moisture. The pixel map 76 and 3-D display map 78 show such a tail 76 adjoining an absorbance peak. The tail 76 and peak 79 exhibit themselves clearly as ridge and peak shapes respectively in the 3-D display map 78. The peak and tail show as a dark concentration area 75 at the peak, and a distinctive streak or tail 76, respectively in the pixel map 76. It will be appreciated that in the pixel map 76, in this exemplary display, the X axis is in the vertical (up and down) and the Y axis is in the horizontal (left to right) of FIG. 6. In the 3-D display map, the Y axis runs from right to left. When the sample or coupon (not shown) was exposed to a corrosive environment, it was held in place with the Y axis of the coupon in a vertical direction (i.e., up for the coupon was towards the left in the pixel map 76, while down was to the right, with the same for the 3-D map 78). The downhill direction where the corrosion product tail formed below a corrosion pit shows clearly as the tail 3 in the pixel map 56 and in the 3-D display 58 each to the right of a corrosion peak. The tail 3 starts at the corrosion pit concentration area forming the peak 2 in the 3-D display map, and a high color density area 4 in the pixel map 76.

Figure 7:
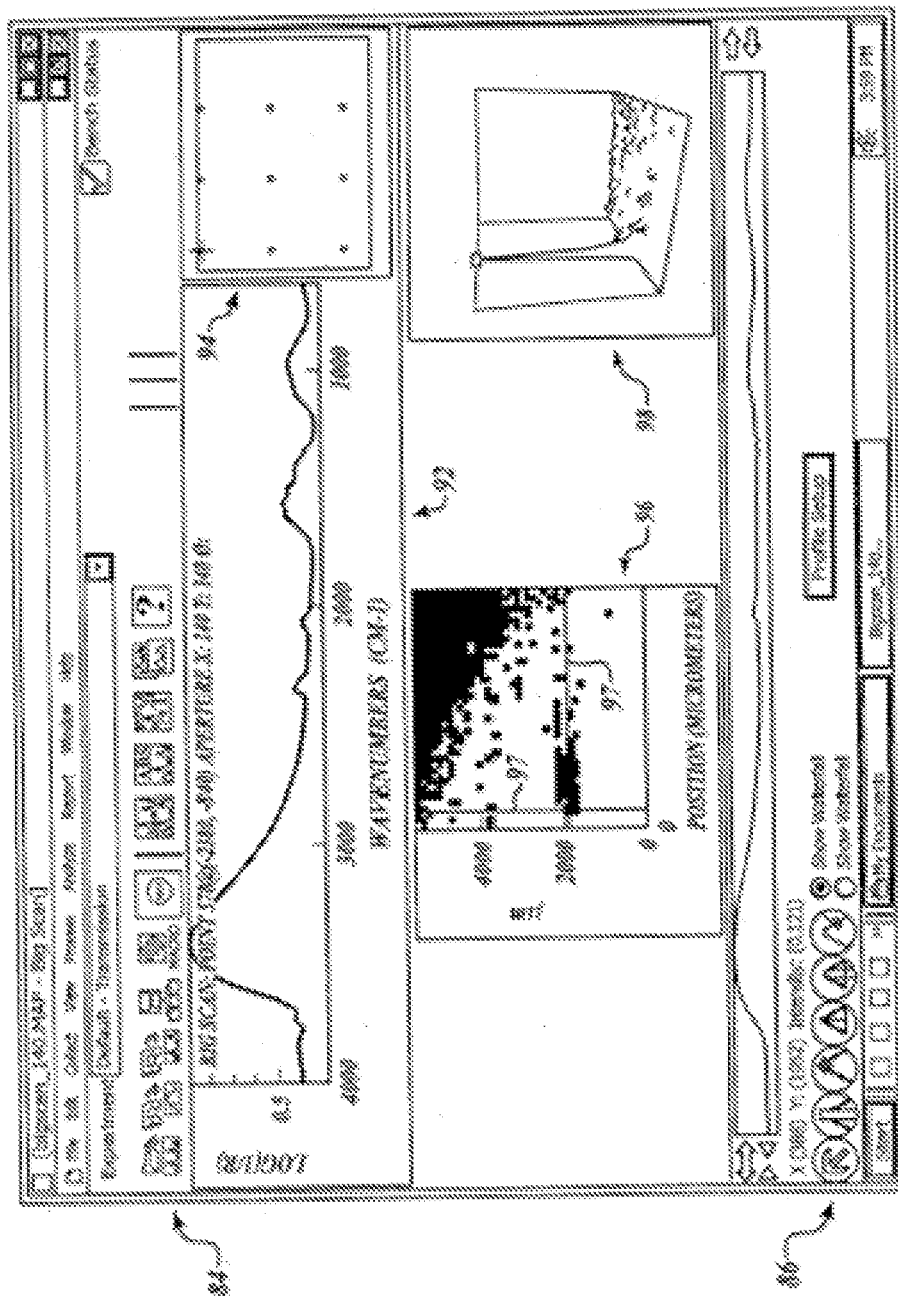

FIG. 7 is a screen shot 80 suitably from a computer program application that may be used in an exemplary embodiment to implement the present invention. The screen shot 80 includes a display of an infrared absorption spectrum 92 at a scan point. It includes an optical display 94 showing a picture of the area around the scan point in the visual spectrum. The screen shot 80 also includes a pixel map 96, and a 3-D contour map 98 displaying absorption levels in the area surrounding the scan point in the manner described in connection with FIGS. 4, 5, and 6. The screen shot 80 is a computer video screen window with choices 84 for performing infrared reflectance absorption spectroscopy and displaying various absorption spectra and data at and around a scan point. The screen shot also includes choices 86 that control the mapping displays for, by way of example and not limitation, the pixel map 96, or a 3-D map 98. In a presently preferred embodiment, the computer program application includes the commercial program application OMNIC/Atlus distributed by ThermoNicolet, in connection with its infrared spectrometers. It will be appreciated that a wide variety of screen and choice configurations may be utilized to implement the present invention, including features that compare absorbance levels to known quantities of corrosion product, and that integrate or summarize areas of absorption at designated wavenumbers and compare the result to a desired standard, such as in a go/no-go test for quality control applications.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A non-destructive method for identifying an amount of corrosion product on a metallic substrate, the method comprising:
   transmitting an infrared beam onto a sample of the metallic substrate;
   collecting a reflected infrared beam reflected by the sample;
   non-destructively determining infrared absorbance (Ia) of the sample at three or more wavenumbers including a first wavenumber, a second wavenumber, and a third wavenumber, wherein the first wavenumber range is within a first band from 800 cm-1 to 1100 cm-1, and the second wavenumber range is within a second band from 1400 cm-1 to 1700 cm-1, and the third wavenumber range is within a third band from 3200 cm-1 to 3600 cm-1;
   correlating the infrared absorbance at the first wavenumber, at the second wavenumber, and at the third wavenumber to an amount of aluminum oxide corrosion on the sample; and
   displaying a map of the amount of corrosion on the sample.

2. The method of claim 1, wherein correlating the infrared absorbance at the first wavenumber and at the second wavenumber to an amount of aluminum oxide corrosion on the sample includes integrating absorbance over a range from 800 cm-1 to 1100 cm-1 and a range from 1400 cm-1 to 1700 cm-1, respectively.

3. The method of claim 1, further comprising: determining a value Is of infrared energy reflected from the metallic substrate having the corrosion product.

4. The method of claim 3, wherein non-destructively determining the infrared energy absorbed in the corrosion product is calculated according to the equation $I_a = -\log_{10}(I_s/I_0)$.

5. The method of claim 1, wherein an infrared microscope collects the reflected infrared beam.

6. The method of claim 1, wherein an array collector collects the reflected infrared beam.

7. The method of claim 1, wherein an infrared spectrometer determines the infrared absorbance.

8. The method of claim 7, wherein a Fourier transform infrared spectrometer determines the infrared absorbance.

9. The method of claim 1, wherein determining the infrared absorbance includes moving the sample relative to a collector such that the reflected infrared beam is collected to determine infrared absorbance of a plurality of areas on the sample.

10. The method of claim 9, wherein moving the sample includes moving a moveable stage linked to the sample.

11. The method of claim 1, wherein determining Ia includes determining absorbance at at least one wave number corresponding with an infrared spectra of the corrosion product.

12. The method of claim 1, wherein the metallic substrate includes an aluminum alloy.

13. The method of claim 12, wherein determining Ia includes determining absorbance for at least one of the first, second, and third wavenumbers corresponding with a peak in absorbance infrared spectrum of an aluminum corrosion product.

14. The method of claim 12, wherein determining Ia includes determining absorbance for at least one of the first, second, and third wavenumbers corresponding with an infrared spectra of one of aluminum oxide and aluminum hydroxide.

15. The method of claim 14, wherein the at least one of the first, second, and third wavenumbers includes at least one of about 950 cm-1, 1640 cm-1, and 3400 cm-1, respectively.

16. The method of claim 1, wherein the first wavenumber is 950 cm-1, the second wavenumber is 1640 cm-1, and the third wavenumber is 3400 cm-1.

17. The method of claim 1, wherein displaying the map includes one of displaying a contour map, displaying a gray-scale map, displaying a color map, and displaying a 3-dimensional projection.

18. A method for quantifying an amount of a corrosion product on a substrate, the method comprising:
   projecting an infrared energy onto at least a portion of the corrosion product on the substrate;
   non-destructively determining an amount of infrared energy absorbed in the corrosion product on the substrate at three or more wavenumbers, including integrating absorbance over a first wavenumber range, and over a second wavenumber range, and over a third wavenumber range, wherein the first wavenumber range is within a first band from 800 cm-1 to 1100 cm-1, and the second wavenumber range is within a second band from 1400 cm-1 to 1700 cm-1, and the third wavenumber range is within a third band from 3200 cm-1 to 3600 cm-1; and
   determining the amount of corrosion product on the substrate by correlating the amount of infrared energy absorbed to a set of predetermined absorption values, including
      correlating the infrared absorbance over the first, second, and third wavenumber ranges to an amount of aluminum hydroxide corrosion on the substrate; and
   displaying the amount of aluminum hydroxide corrosion on the substrate.

19. The method of claim 18, wherein determining the amount of infrared energy absorbed includes moving the sample relative to a collector such that a reflected infrared beam is collected to determine infrared absorbance of a plurality of areas on the substrate.

* * * * *